(12) United States Patent
Braband et al.

(10) Patent No.: US 6,906,234 B1
(45) Date of Patent: Jun. 14, 2005

(54) CONTINUOUS METHOD AND HEAT PUMP DEVICE FOR ENRICHING LIQUID LOW-CONCENTRATED REACTION MIXTURES

(75) Inventors: Jürgen Braband, Leipzig (DE); Peter Müller, Leipzig (DE); Rüdiger Bernhardt, Plodda (DE); Andreas Otto, Jessnitz (DE)

(73) Assignee: Symrise GmbH & Co. KG (DE)

( * ) Notice: Subject to any disclaimer, the term of this patent is extended or adjusted under 35 U.S.C. 154(b) by 0 days.

(21) Appl. No.: 09/762,168

(22) PCT Filed: Jul. 30, 1999

(86) PCT No.: PCT/DE99/02347

§ 371 (c)(1),
(2), (4) Date: Feb. 26, 2001

(87) PCT Pub. No.: WO00/07967

PCT Pub. Date: Feb. 17, 2000

(30) Foreign Application Priority Data

Aug. 4, 1998 (DE) .......................................... 198 35 203

(51) Int. Cl.$^7$ ............................ C07C 7/00; B01D 3/00; B01D 1/00
(52) U.S. Cl. .......................... 585/809; 585/643; 203/26; 159/24.1; 159/24.2; 159/24.3
(58) Field of Search ............................... 159/24.1, 24.2, 159/24.3; 203/26; 585/809, 643

(56) References Cited

FOREIGN PATENT DOCUMENTS

| EP | 343437 | 11/1989 |
|---|---|---|
| GB | 1105565 | 3/1998 |

*Primary Examiner*—Thuan Dinh Dang
(74) *Attorney, Agent, or Firm*—Pendorf & Cutliff

(57) ABSTRACT

A continuous method and a heat pump device for enrichment of low-concentrated reaction mixtures resulting from the production of cycloalkanedienes by means of catalytic metathesis of cyclic aliphatic alkenes and cyclooligomers in organic reaction media with reduced energy consumption. Using the heat pump principle, liquid reaction mixtures with a content of at least 0.1 w/w % are enriched in an organic reaction medium to 30 to 50 w/w %. The organic reaction medium at temperature T1 is evaporated in an evaporator, the vapor is withdrawn and compressed to temperature T2 in a compressor, at a pressure difference of 0.25 to 1 bar. Compressed vapor of the reaction medium transfers heat energy obtained from electric energy in the heat exchanger of the evaporator to the organic reaction medium at temperature T1, and the temperature difference (T2−T1) does not exceed 12 K.

9 Claims, 1 Drawing Sheet

Figure 1:
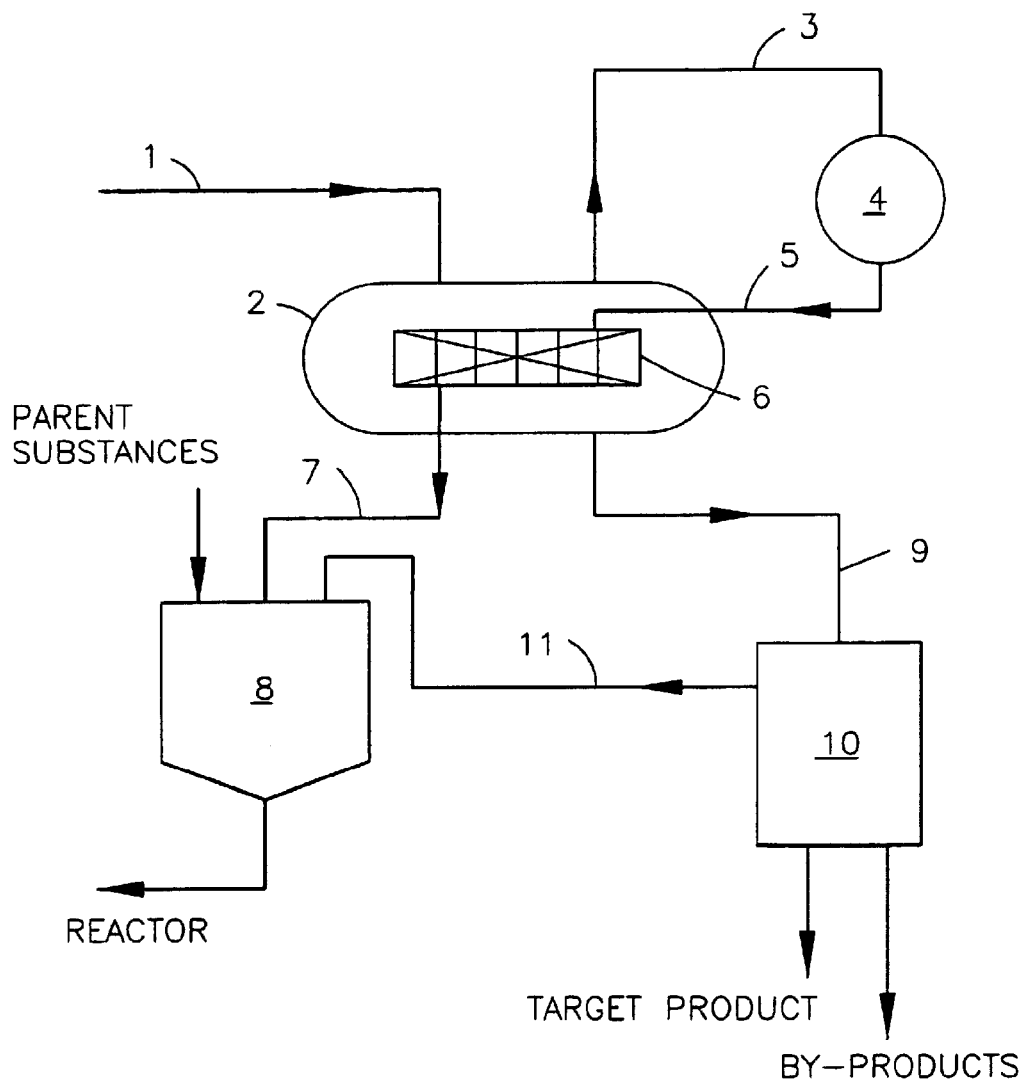

CONTINUOUS METHOD AND HEAT PUMP DEVICE FOR ENRICHING LIQUID LOW-CONCENTRATED REACTION MIXTURES

The reaction relates to a continuous method and a heat pump device for enrichment of low-concentrated reaction mixtures resulting from the production of cycloalkanedienes by means of catalytic metathesis of cyclic aliphatic alkenes and cyclooligomers in organic reaction media.

Valuable musk odorous substances are synthetically manufactured out of cycloalkanedienes with a ring size between 12 and 18 C atoms favouring 16 C atoms, i. e. cyclohexadiene.

The production of cycloalkanedienes, especially cyclohexadekadiene is described in GB-A 1105565 (1), EP-A 0192333 (2), and EP-B 0343437 (3). After the described method, starting out from cyclic alkenes with 6 to 9 C atoms (1,2) or cyclopolyoctenylene (3) with a degree of polymerisation $\geq 3$ cycloalkanedienes are formed, if parent substances of a metathesis reaction are converted in liquid phase at a supported catalyst on basis of $Re_2O_7/Al_2O_3$ (1,2) or at a modified supported catalyst.

In (2) for the first time it is mentioned, that the selectivity of target products and with that the efficiency can be increased, if the metathesis reaction does not exceed the dimerisation stage. This is possible by working with highly diluted solutions of parent substances (0.01 to 0.05 molar).

As metathesis-inert solvents for the dilution of parents aliphatic alkanes like pentane, hexane, heptane, cyclopentane, cyclohexane, petroleum ether, chlorinated hydrocarbons like methylene chloride, chloroform, carbon tetrachloride, or aromatics like chlorobenzene and m-dichlorobenzene are used (2,3).

After flowing through the catalyst bed a low-concentrated reaction mixture in organic solvent is received containing the target product, by-products and unconverted parent substances.

According to (2,3) the reaction mixture leaving the reactor is put on a distillation device and separated into its components. This way the target product is received as relatively high-boiling fraction, while the low-boiling solvent as well as occasionally unconverted parent substances are recycled, after supplying new parent substances they are fed back into the reactor.

To increase the selectivity of the metathesis reaction in view of target products cycloalkanedienes with 12 to 18 C atoms working in highly diluted solutions with a ratio parent substance: solvent of 1:1300 is absolutely required.

This fact is the essential disadvantage of this method, till now considerably limiting or preventing the technical realisation of the method. Separating the reaction solution by means of batch distillation as usual into target product and solvent requires high energy for evaporation of the solvent and increases the costs for the production of the target product and this way also the price of the synthetic odorous substance considerably.

Thus, the task is to find a method to lower the energy costs for the separation of the reaction solution into target product, by-products, and organic reaction medium (solvent) considerably and to recycle the organic reaction medium at the same time.

Now a method has been found to solve the above mentioned task by applying the principle of a heat pump in such a way, that the heat level of the organic reaction medium is permanently increased and decreased within a narrow temperature range and no permanent evaporation and condensation is required. This target is achieved by means of a suitable connection of heat exchangers in combination with a vent compressor. Electric energy is converted into heat via a vent compressor, thus the organic reaction medium is compressed and heated. The heat absorbed in the vent compressor is directly applied for evaporating the organic reaction medium out of the prevailing reaction mixture in the heat exchanger, thus a new cycle starts.

While elements of the method are known the combination of these elements as an inventive method so far has not been applied in odorous substance chemistry.

The method to resolve above mentioned task is characterised by the features of claims 1 to 4 and can be executed by means of the device described in claim 5.

The low-concentrated reaction mixture in the organic reaction medium is continuously fed. via a feeding line (1) into a single or multiple chambered condenser with temperature T1.

This temperature is determined by the reaction conditions of the catalytic metathesis reaction, especially by the infusibility of the catalyst, the selectivity of the catalytic reaction with regard to conversion of parent substances to the target product depending on temperature and the organic reaction medium applied in connection with that. Boiling points of aliphatic, cyclic aliphatic, and chlorinated hydrocarbons stated in claim 2 are in a range between 30° C. and 120° C. With regard to the aim to keep energy expenses for the enrichment of the reaction mixture in the organic reaction medium as low as possible the organic reaction medium has to be chosen in such a way, that its boiling point is just a few centigrade above the reaction temperature of parent substances at the catalyst.

For that reason the organic reaction medium has to be chosen in such a way the temperature difference between entry temperature T1 of the reaction solution in the evaporator and the boiling point of the organic reaction medium to be evaporated does not exceed 5 K.

By enriching the reaction mixture in the organic reaction medium the boiling point of the applied solvent is increasing. The boiling point curve shows, that the boiling point of the solvent increases significantly, when the reaction mixture in the organic reaction medium is enriched to more than 50 w/w %. Depending on actual conditions of the method the energetic demand is lowest when the reaction mixture in the evaporator is enriched in the organic reaction medium to 30 to 50 w/w %.

From the evaporator the vapours of the organic reaction medium are sucked off and compressed, which raises the temperature to T2. The pressure difference is chosen in such a way, that the temperature T2 is 5 to 12 K above T1.

This is achieved by a pressure difference of 0.25 to 1.0 bar. The vapour of the organic reaction medium compressed to temperature T2 is fed back to the heat exchanger of the evaporator and transfers the absorbed heat energy to the organic reaction medium being in the evaporator at temperature T1, which, as a result, is evaporating. This heat exchange is most economical, if the temperature difference between T1 and T2 does not fall below 5 K, preferably between 8 and 12 K.

Applying the described method low-concentrated liquid reaction mixtures with a content of 0.1 w/w % at least in the organic reaction medium are enriched with lower energy demand to 30 to 50 w/w % in the evaporator.

The reaction mixture enriched to that percentage of valuable product is permanently sucked off via pipe (9) from the evaporator and fed to the distillation plant (10) for further separation into organic reaction medium, unconverted parent substances, by-products and target product. Organic reaction medium and unconverted parent substances are again unified in vessel (8) with the organic reaction medium condensed in the heat exchanger (6) of the evaporator (2), added to parent substances and fed into the reactor.

Applying the inventive method energy consumption for the evaporation of the organic reaction medium can be lowered by 80%, expenses by about 30%. The following example will explain the method practically.

EXAMPLE

A reaction mixture from the reactor with a content of valuable product of 0.34 w/w % containing 2 w/w % of cyclooctene, 30 w/w % of cyclohexadekadiene, and 60 w/w % of oligomers in n-hexane is continuously fed into a multiple-chamber evaporator. At an evaporator efficiency of about 17,000 kg/h n-hexane the content of valuable product mixture in the evaporator is increased to 35 w/w %.

The entry temperature amounts to 67° C. The boiling point of n-hexane amounts to 68.5° C. By increasing the concentration of the valuable product mixture in n-hexane up to 35 w/w % the boiling point of the mixture in the evaporator increases to 72° C. (T1). In the compressor n-hexane vapour is compressed by means of a pressure difference of 0.41 bar which increases the temperature to 81° C. (T2). This way T2 minus T1 amounts to 9 K.

The compressed n-hexane vapour is lead through the heat exchangers of the evaporator and transfers heat energy to n-hexane of temperature T1. After that condensed n-hexane goes from heat exchanger into the mixture vessel.

At the above mentioned evaporation of n-hexane continuously 165 kg/h of reaction mixture enriched to 35 w/w % are sucked off from the evaporator. The share of the valuable product mixture is 57.5 kg. Energy consumption is about 100 kW/h.

Legend to FIG. 1:
1 feeding pipe
2 evaporator
3 suction pipe
4 compressor
5 pressure pipe
6 heat exchanger
7 pipe
8 mixing vessel
9 pipe
10 high-grade distillation plant
11 pipe

What is claimed is:

1. Continuous method for enrichment of reaction mixtures of unconverted parent substances, a target product, and by-products, the reaction mixtures comprising a concentration of at least 0.1 w/w % resulting from the catalytic metathesis of cycloalkanedienes from mixtures of cyclic aliphatic alkenes and cyclooligomers in a liquid organic reaction media, wherein said media is an aliphatic, cyclic aliphatic or chlorinated hydrocarbon, in which the liquid organic reaction media and the unconverted part of parent substances are recycled, for the use as heat transfer medium at a temperature difference of 5 K at least (T1/T2) evaporated and compressed, and finally are fed in condensed state to a mixing vessel for adjusting the concentration ratios of parent substances, said method comprising the steps of:

(a) continuously withdrawing a low-concentrated reaction mixture from a reactor and feeding said mixture into a single or multiple chambered evaporator at temperature T1;

(b) sucking vapors of the organic reaction medium from the evaporator;

(c) compressing said vapors in a vent compressor by means of electrical energy;

(d) feeding back said compressed vapors at temperature T2 into a heat exchanger of the evaporator;

(e) performing heat exchange in the evaporator between the low-concentrated reaction mixture at temperature T1 and the compressed organic reaction medium at temperature T2, (f) continuously feeding back condensed organic reaction medium from the heat exchanger of the evaporator into a mixing vessel for adjusting the method determined concentration ratios; and (g) continououesly withdrawing reaction medium enriched with reaction mixture to a content of at least 30 w/w % from the evaporator, wherein said reaction medium comprises target product, by-products, parent substances and organic reaction medium.

2. The method according to claim 1, wherein said liquid organic reaction media comprises pentane, hexane, heptane, cyclopentance, cyclohexane, cycloheptane, methylene chloride, chloroform, carbon tetrachloride, petroleum ether, or a mixture thereof.

3. The method according to claim 1 or claim 2, wherein temperature T1 is less than 5 K below of the boiling point of the liquid organic reaction medium.

4. The method according to claim 1 or claim 2, wherein the temperature difference between T1 and T2 is from about 8 to about 12 K.

5. A device for the continuous enrichment of a reaction mixture according to the method of claim 1, said device comprising:

(a) a feeding pipe (1) for feeding low-concentrated reaction mixture comprised in a liquid organic reaction medium, (b) a single or multiple-chambered evaporator (2) including a heat exchanger (6), in which the liquid organic reaction medium evaporates and target product, by-product, and parent substance components of the reaction mixture are enriched, (c) a suction pipe (3) to feed the vapor of the organic reaction medium to the compressor (4), (d) a compressor (4) to compress the vapor of the organic reaction medium and to heat it to temperature T2, (e) a pressure pipe (5) to feed the compressed and heated organic reaction medium to the heat exchanger (6), (f) a heat exchanger (6) inside the evaporator (2) for transfer of heat between the liquid organic reaction medium as well as the reaction mixture with temperature T1 and the compressed organic reaction medium with temperature T2, and (g) a pipe (7) to carry the condensed organic reaction medium from heat exchanger (6) to mixing vessel (8).

6. The method of claim 1 further comprising the step of:
(h) feeding the enriched reaction mixture into a high-grade distillation plant to distill off the residual part of the organic reaction medium and to separate the reaction mixture into target product, by-products, and parent substances.

7. The method of claim 6, further comprising the step of:
(i) feeding back a condensed organic reaction medium and said parent substances to the mixing vessel according to (f).

8. The device of claim 5, further comprising a high-grade distillation plant (10) for the separation of the enriched reaction mixture into target product, by-products, parent substances, and organic reaction medium, and a pipe (9) to carry the enriched reaction mixture from evaporator (2) to the high-grade distillation plant (10).

9. The device of claim 8, further comprising a pipe (11) to carry the liquid organic reaction medium from the distillation plant (10) to the mixing vessel (8).

* * * * *